United States Patent [19]

Delpy et al.

[11] 4,396,017
[45] Aug. 2, 1983

[54] TRANSCUTANEOUS GAS SENSOR

[75] Inventors: David T. Delpy; Dawood Parker, both of London, England

[73] Assignee: Vickers Limited, London, England

[21] Appl. No.: 228,678

[22] Filed: Jan. 26, 1981

[51] Int. Cl.³ .............................................. A61B 5/00
[52] U.S. Cl. .................................... 128/635; 128/639
[58] Field of Search ....................... 128/635, 639, 632; 204/195 B, 195 P

[56] References Cited

U.S. PATENT DOCUMENTS 4,311,151  1/1982  Hagihara .............................. 128/635

FOREIGN PATENT DOCUMENTS 2346716  10/1977  France ................................. 128/635

Primary Examiner—Richard J. Apley
Assistant Examiner—T. J. Wallen
Attorney, Agent, or Firm—Pearne, Gordon, Sessions, McCoy, Granger & Tilberry

[57] ABSTRACT

A transcutaneous gas sensor for application to the body surface of a patient is provided. The sensor includes a sensing electrode having an exposed surface region which, in use, is applied to the body surface of the patient with an electrolyte layer between the electrode and the patient's body. Gas which has diffused through the patient's body from his blood to the body surface results in an electrochemical reaction taking place at the exposed surface region of the electrode. This exposed surface region can consist of an individual surface area, or several such surface areas. In one embodiment, the surface area or areas are arranged and are of a configuration such as to have associated therewith an imaginary envelope of greater area than the total area occupied by the individual surface area or areas; with such an arrangement, the surface area or areas have the same or similar widths. In a second embodiment, the or each exposed surface area(s) of the electrode has a sufficiently small width dimension and is shaped and arranged so that the depletion zone set up in the electrolyte layer when the sensor is in use is confined to a depth not exceeding about 1 mm. The flow of gas from the patient's blood to his body surface can be encouraged by local heating of the area under investigation. Detection of the current flowing through the electrode as a result of the electrochemical reaction in the electrolyte layer provides a measure of the gas partial pressure in the patient's blood.

7 Claims, 8 Drawing Figures

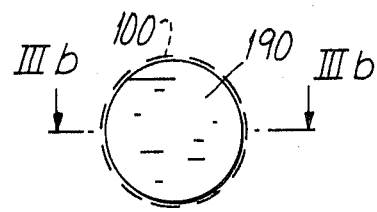
Fig.3a.
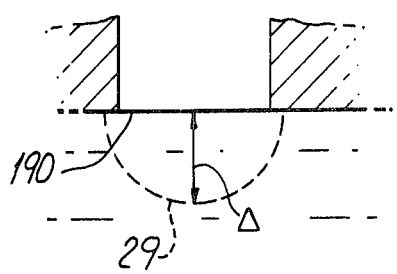
Fig.3b.
Fig.4a.
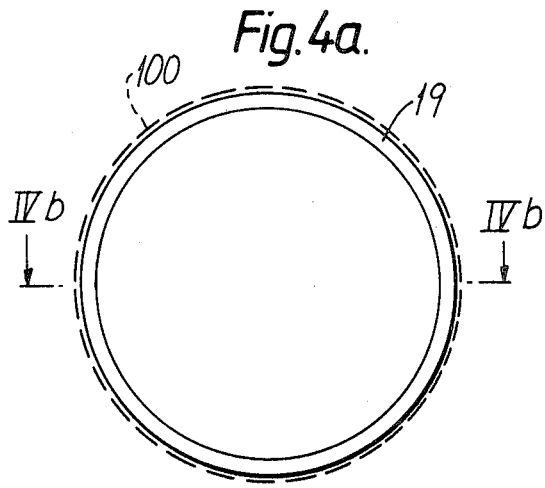
Fig.4b.
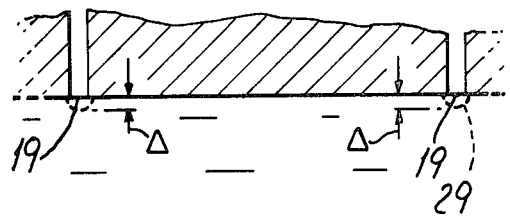
Fig.5a.
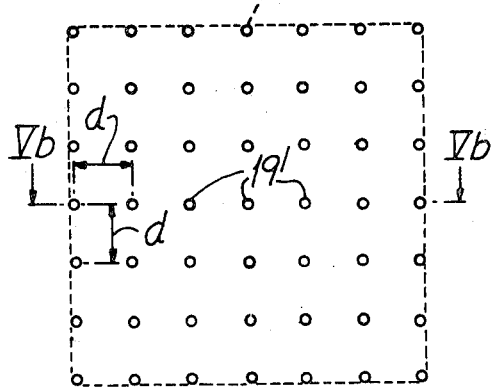
Fig.5b.
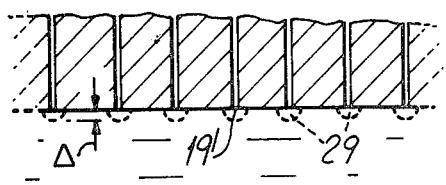

TRANSCUTANEOUS GAS SENSOR

This invention relates to a transcutaneous gas sensor.

It is well known that gas (mainly oxygen and carbon dioxide) in capillary blood diffuses through to the surface of the patient's body, the diffusion rate being proportional to the capillary gas level. In British Pat. No. 1,312,169 there is disclosed a transcutaneous gas sensor in which a heating device serves to raise the temperature of a patient's body surface in the region in which the sensor is applied to the patient's body. This has the effect of thermally stimulating the capillary blood circulation in the patient's body close to the region of increased temperature, thereby raising the gas level in the capillaries to a value near that existing in aerterial blood. The gas diffusing through the skin to the skin surface passes through an electrolyte layer to a cathode, on an exposed surface of which an electrochemical reaction takes place, usually when a suitable potential is applied to the cathode. The current generated owing to the electrochemical reaction is measured to provide an indication of the partial pressure of the gas in the capillary bloodstream, which is closely similar to that of the gas in the arterial bloodstream owing to the thermal stimulation.

In one form the exposed surface of the cathode is circular. However, the rate at which the cathode would consume the diffused gas would be greater than the rate at which gas would be made available at the skin surface and this would affect the accuracy of the readings taken with the gas sensor. Therefore, the sensor includes a membrane, permeable to the diffused gas, which traps the electrolyte layer against the cathode and, with the sensor applied to the patient's skin, serves to restrict the rate of consumption of the diffused gas by the cathode to a suitable value. On the other hand, the use of the membrane means that the membrane has to be removed and re-fitted to the sensor body each time the electrolyte layer (a gel) is changed. Also the response characteristics of the sensor can change slightly with time owing to factors such as creep, relaxation and thermal expansion of the membrane material. Furthermore, using a membrane increases the response time of the gas sensor, and in some instances this can be undesirable, especially when the thickness of the membrane is comparatively large.

By reducing the cathode exposed surface area, the ability of the cathode to consume gas is reduced, so the thickness of membrane required is reduced, thereby allowing the response time of the sensor to be reduced. However, there is a limit to how thin the membrane can be made without impairing its strength, with consequent risk of rupture and instability of the gas sensor in operation.

The present invention starts from an appreciation that the exposed surface area could be reduced still further so that the gas consumption rate of the cathode, even in the absence of any membrane, is less than the rate at which diffused gas is made available at the skin surface. There is then no need for a membrane with the attendant drawbacks mentioned above. However, further difficulties will then arise. Firstly, for a cathode with, for example, a circular exposed surface, the exposed surface area will be sufficiently small that any dust or dirt present when taking a measurement can "mask" the cathode and thereby significantly modify the accuracy of the measurements taken. The current generated when using a small cathode exposed surface area is also small, and can in some cases be hard to measure. Thirdly, (and even in cases where a membrane is present) there is the added requirement that the depletion zone in the electrolyte layer below the exposed surface region of the cathode should not extend from the electrolyte layer into the patient's body as, otherwise, the partial pressure profile in the skin is altered and this would affect the accuracy of the measurements taken. In the absence of a membrane, for a given electrode size and configuration the above requirement will dictate the minimum electrolyte layer needed, whereas ideally the electrolyte layer should be as thin as possible to minimise the response time of the sensor.

According to the invention from one aspect, a transcutaneous gas sensor for application to a body surface of a patient comprises a sensing electrode having an exposed surface region so that, with an electrolyte layer between said surface region and said body surface in use of the sensor, an electrochemical reaction can take place on said exposed surface region in the presence of gas which has diffused through the patient's body from the blood to the body surface, the exposed surface region consisting of at least one individual surface area, the surface area or areas being so arranged and of such configuration as to have associated therewith an imaginary envelope in which the area bounded by the envelope is large compared with the total area occupied by the surface area or areas, the surface area or areas having the same or similar widths.

According to the invention from a second aspect a transcutaneous gas sensor for application to a body surface of a patient comprises a sensing electrode having an exposed surface region and a layer of electrolyte thereon so that, with the sensor applied to said body surface, an electrochemical reaction can take place on said exposed surface region in the presence of gas which has diffused through the patient's body from the blood to the body surface, the exposed surface region consisting of at least one individual surface area, the such surface area or areas having a sufficiently small width dimension, and the shape and arrangement of the surface area or areas being such, that the depletion zone set up, in use, in the electrolyte layer is confined to a depth not exceeding approximately 1.0 mm.

Preferably, the gas sensor will further comprise a heating device arranged to effect local thermal stimulation of the blood circulation close to the body surface when the sensor is applied to the body surface. In one construction the gas sensor also comprises a body part, carrying the heating device and the electrode, and a mounting part on which the body part is mounted and which has an application surface for application to the patient's body, the mounting part having an opening formed therein for containing a or said layer of electrolyte between the body surface of the patient and the exposed surface region of the electrode. The arrangement and dimensioning of the application surface and opening relative to those of the exposed surface region should be such that the rate of gas consumption by the electrode does not exceed the rate at which gas is made available to the sensor at the skin surface.

Generally, the width of the or each individual surface area will be in the range 0.01 microns to 5 microns and a typical value is 0.5 microns. When the electrode has a single exposed surface area, that area may be in the shape of a spiral band, a circular band, a zig-zag band or a polygonal band, for example. Alternatively, the exposed surface region may consist of a plurality of individual surface areas, for example arranged in a matrix configuration. In the case of a single exposed surface area having adjacent successive sections (e.g. successive turns of a spiral or successive sections of a zig-zag), the spacing between adjacent sections is preferably such that there is no substantial overlap of the separate depletion zones set up in the electrolyte by the sections concerned. This minimises the greatest depth of the depletion zone. The same consideration applies in respect of adjacent surface areas in the case of the exposed surface region being constituted by several individual surface areas. Conveniently, the electrode can be formed by applying electrically conductive material around the peripheral surface of an insulative core part by a vacuum deposition process, and then applying a sleeve of insulative material around the vacuum deposited conductive material, so as to provide a thin exposed band in the approximate shape of a ring at each end of the resulting assembly, one of which bands constitutes said exposed surface region of the electrode.

For a better understanding of the invention and to show how the same may be carried into effect, reference will now be made by way of example, to the accompanying drawings in which:

FIG. 3a is a front view of the exposed surface area of a cathode included in a gas sensor which is not in accordance with the invention;

FIG. 3b is a sectional view taken along the line IIIb—IIIb of FIG. 3a showing in particular the depth of the depletion zone below the cathode;

Figure 1:
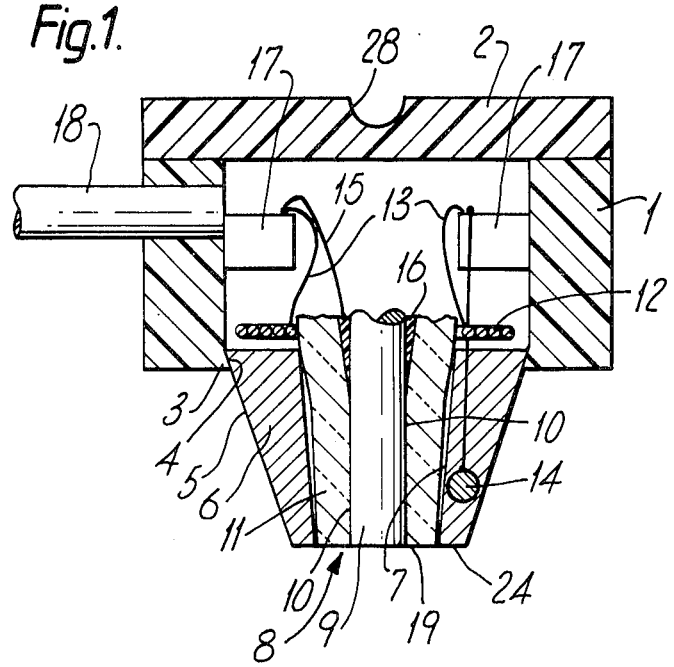
FIG. 1 is a rather diagrammatic vertical sectional view through one form of transcutaneous gas sensor in accordance with the invention.

FIGS. 4a and 4b are views, corresponding to FIGS. 3a and 3b respectively, but in the case of the cathode included in the FIG. 1 embodiment, and FIGS. 5a and 5b are views again corresponding to FIGS. 3a and 3b respectively, but in the case of a cathode having several individual exposed surface areas.

Referring to FIG. 1, the transcutaneous gas sensor comprises a body suitably of plastics material consisting of a cylindrical part 1 and a disc-shaped cover 2 secured to the upper end of the part 1. The lower end is formed with an inwardly projecting flange 3 formed with a conically tapering seating surface 4 against which is seated the outer, part-conical, surface 5 of a silver reference electrode (anode) 6 which is formed with a central bore 7 in which is mounted a cathode assembly 8. This assembly consists of a central cylindrical rod 9 of electrically insulative material such as glass. A very thin layer of high purity electrically conductive material (e.g. gold) 10 is provided around the peripheral surface of the glass rod 9, suitably by a vacuum deposition technique. Alternatively, it would be possible to form the thin layer by an etching process. A culindrical sleeve 11 of insulative material, which again can conveniently be glass, is positioned or shrunk around the gold cathode to complete the cathode assembly. The resulting thin circular band 19 of gold (FIG. 4a) at the lower end face of the cathode assembly consitutes a measuring surface exposed to the gas diffused from the patient's body while measurements of the partial pressure of the gas are being taken.

A circular "pancake" heater 12 is mounted in thermal contact with the upper end face of the anode 6 and is supplied via electrical connection wires 13. A thermistor 14 is disposed within the material of the anode close to the lower end thereof and is connected in the heater supply circuit so as to maintain the temperature of the anode as closely as possible to a predetermined temperature value. A further wire 15 leads to a small annular gap provided between the central rod 9 and sleeve 11 in the upper region of the cathode assembly, this gap being filled with electrically conductive material 16, for example conductive epoxy resin, which provides an electrical connection between the lead 15 and the gold cathode 10. The wires 13, 15, as well as the anode 5, are connected to suitable connection points on a terminal board 17 disposed within the cylindrical part 1 and a cable 18 provides the required connections between the terminal board and the external electrical supply and measuring equipment.

Figure 2:
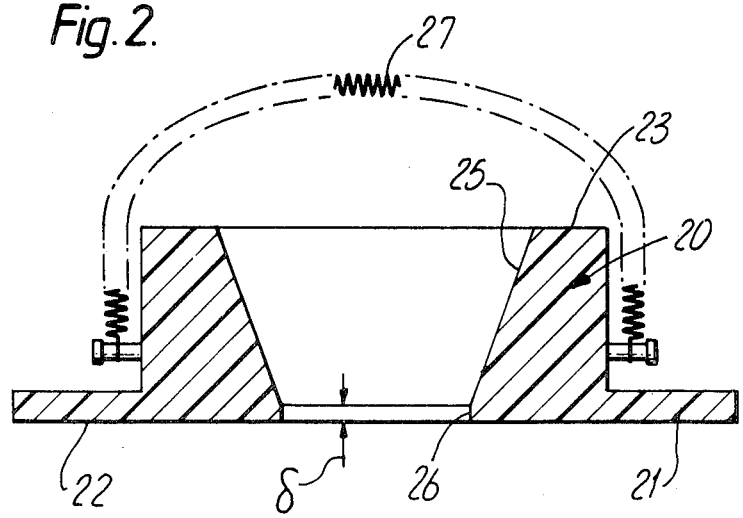
FIG. 2 shows a vertical sectional view through a mounting ring to enable the gas sensor to be applied to a patient's skin.

Referring to FIG. 2, there is shown a mounting ring 20 having a lower flange 21 providing an application surface 22 for application to the patient's body. The upper end face 23 of the ring 20 serves as a seating for the lower end face 24 (FIG. 1) of the cylindrical part 1, the part-conical surface 5 then being arranged at a small spacing from a correspondingly-shaped inner surface 25 of the mounting ring and the exposed surface region 19 of the cathode then lying in a plane at a small spacing $\delta$ from the plane of the application surface 22. A central opening 26 is formed in the mounting ring for containing a gelled electrolyte between the patient's skin and the exposed surface region 19. A retaining spring 27 is attached at both ends to opposite sides of the mounting ring 20 and is intended to be fitted around the top of the unit shown in FIG. 1. A groove 28 (FIG. 1) for the retaining spring is preferably formed in the cover 2.

In use, the opening 26 is filled with gelled electrolyte and the transcutaneous gas sensor applied to the patient's body and is held in position in a suitable convenient manner, such as with the use of a double sided adhesive disc. The space between the surface 5 of the electrode 6 and the correspondingly-shaped surface 25 of the mounting ring is provided to accommodate excess electrolyte squeezed out of the space between the patient's skin and the underside of the gas sensor, bounded laterally by the opening 26. Local thermal stimulation of the blood circulation in the region of the gas sensor due to the predetermined elevated temperature of the anode 5 maintained by the thermistor-controlled heating circuit maximises the rate at which diffused gas from the bloodstream is made available at the skin surface, and thereby also the rate at which the gas arrives at the exposed surface region of the cathode. The total area of the exposed surface region relative to the skin area from which diffused gas is passing to the cathode (this skin area depending on the size and arrangement of the central opening and application surface of the mounting ring) is such that the rate of consumption of gas by the cathode does not exceed the rate at which the diffused gas is made available to the gas sensor.

Generally, the depth of the depletion zone, which should be confined to the thickness of the electrolyte layer, will increase for larger widths of the circular band 10, and thicker electrolyte layers lengthen the response time of the gas sensor. In order to give a response time which is not unduly long, a suitable range for the width of the band is 0.01 to 5 microns, and a typical width for the band 19 is 0.5 microns. It is because the maximum width of the band is so small that the aforementioned vacuum deposition process is especially suitable for fabricating the gold layer. FIGS. 3a, 4a and 5a show examples of configuration for the exposed surface region of the cathode, in each of which examples it is assumed that the rate of gas consumption is the same (and less than the rate of supply of diffused gas from the bloodstream), although the scales adopted in these Figures, whilst having been chosen to assist a full understanding of the considerations involved, are not intended necessarily to be exactly in the appropriate relative proportions compatible with the stated assumption. Only FIGS. 4a and 5a, however, fall within the cope of the invention. In FIG. 3a the exposed surface region is a single circle 190, and in FIG. 4a it is a circular band 19, as already described, but in FIG. 5a the exposed surface region consists of a matrix of individual circular areas 19'. In each of FIGS. 3b, 4b and 5b, the greatest depth $\Delta$ of the depletion zone 29 below the exposed surface region is shown. This depth is generally slightly larger (by perhaps 10 or 20 microns) than the width of the or each individual exposed surface area. To meet the requirement that the depletion zone should be confined to the depth of the electrolyte layer, the thickness of this layer must be greater than $\Delta$. However, in the FIGS. 3a, 3b example, the resulting electrolyte layer would be so large, relatively speaking, that only a comparatively slow response time could be achieved from the gas sensor, which would be unacceptable for most purposes. On the other hand, $\Delta$ in the FIGS. 4a, 4b and 5a, 5b examples is very much smaller and a more than adequate response time results.

In each of FIGS. 3a, 4a and 5a, reference numeral 100 denotes an imaginary envelope with which the exposed surface area or areas (190, 19 or 19') of the cathode is associated in each case. It will be seen that in FIGS. 4a and 5a, in contradistinction to FIG. 3a where the area bounded by the envelope is equal to the area occupied by the exposed surface area 190, the corresponding bounded areas (a circle and a square respectively) are comparatively large in proportion to the total annular area of the band 19 in FIG. 4a and the total area occupied by the individual surface areas 19' in FIG. 5a. Because of this and with suitable choice of an appropriate electrolyte (the electrolyte chosen can have some effect on the performance of the gas sensor, dependent upon the diffusivity properties of the electrolyte), only a comparatively thin electrolyte layer giving good response time performance is necessary to accommodate the depletion zone. If in a modification of FIG. 5a not forming part of the invention the rows and columns of circular areas 19' were to be rearranged so that each area 19' would touch the immediately neighbouring areas 19' tangentially, the depletion zones associated with the individual surfaces 19' would overlap one another so that the composite depletion zone would extend much further down below the underside of the cathode assembly, resulting in an unacceptably high response time having regard to the thickness of the electrolyte layer. It will be noted that in this modification, the total area occupied by the several areas 19' is not significantly different from the area bounded by the associated imaginary envelope. Preferably, in the FIGS. 5a, 5b arrangement, the inter-row and -column spacing d is not less than about 10 times the diameter of each circular area 19', so as to avoid any overlap of the depletion zones 29 set up by the individual exposed surface areas 19'. Bearing in mind the conflicting requirements of minimising the electrolyte thickness to increase response time while ensuring that the depletion zone is confined to the electrolyte layer, and also the fact that a skin surface is not usually flat, an overall compromise is to make the depth of the recess 26 in the mounting ring 20 equal to about 0.5 mm. Providing the electrolyte layer does not have to accommodate a depletion zone depth exceeding approximately 1.0 mm, an acceptable response time for the sensor can result. However greater depletion zone depths yield unacceptably high response times.

It should also be noted that in FIGS. 4a and 5a the surface areas 19, 19' have in each case the same widths. Comparatively small variations in the widths can still provide perfectly acceptable results, but large ones do not. For example, if in a modification again not forming part of the invention, one of the areas 19' were enlarged so as to touch the immediately neighbouring areas 19', the depletion zone depth below that one area 19' would be unacceptably large.

It is also pointed out that an acceptable measuring current is produced in the cathode of the FIGS. 4a, 5a embodiments, despite the comparatively small area of each individual exposed surface area of the cathode, since the individual small currents due to the electrochemical reactions on the several exposed surface areas collectively produce an easily measurable cathode current.

In a modification, the reference electrode could be omitted from the gas sensor, a separate reference electrode attached to some other part of the patient's body then being used to complete the measuring circuit. Also, the heating device is not essential since without it transcutaneous measurements can still be made of the capillary gas partial pressure, but for the reasons given above in the opening passages of the specification, arterial measurements with the gas sensor require the use of thermal stimulation.

What is claimed is:

1. A transcutaneous gas sensor for application to a body surface of a patient, which comprises a sensing electrode having an exposed surface region so that, with an electrolyte layer between said surface region and said body surface in use of the sensor, an electrochemical reaction can take place on said exposed surface region in the presence of gas which has diffused through the patient's body from the blood to the body surface, the exposed surface region consisting of at least one individual surface area, the surface area being so arranged and of such configuration as to have associated therewith an imaginary envelope in which the area bounded by the envelope is large compared with the total area occupied by the surface area, said electrolyte layer being disposed intermediate said surface area and said body surface, said electrolyte layer having a predetermined thickness and opposed sides respectively in direct contact with said surface area and said body surface, said direct contact between said electrolyte layer and said sensing electrode being substantially limited to said surface area.

2. A transcutaneous gas sensor for application to a body surface of a patient, which comprises a sensing electrode having an exposed surface region and a layer of electrolyte thereon so that, with the sensor applied to said body surface, an electrochemical reaction can take place on said exposed surface region in the presence of gas which has diffused through the patient's body from the blood to the body surface, the exposed surface region consisting of at least one individual surface area, such surface area having a sufficiently small width dimension, and the shape and arrangement of the surface area being such, that the depletion zone set up, in use, in the electrolyte layer is confined to a depth not exceeding approximately 1 mm, said electrolyte layer being disposed intermediate said surface area and said body surface, said electrolyte layer having a predetermined thickness and opposed sides respectively in direct contact with said surface area and said body surface, said direct contact between said electrolyte layer and said sensing electrode being substantially limited to said surface area.

3. A sensor as claimed in claim 1 or 2, which further comprises a heating device arranged to effect local thermal stimulation of the blood circulation close to the body surface when the sensor is applied to the body surface.

4. A sensor as claimed in claim 3, which comprises a body part carrying the heating device and the electrode, and a mounting part on which the said body part is mounted and which has an application surface for application to the patient's body, the mounting part having an opening formed therein for containing said layer of electrolyte between the body surface of the patient and the exposed surface region of the electrode.

5. A sensor as claimed in claim 1 or 2, wherein said surface area is in the shape of a spiral band, a circular band, a zig-zag band or a polygonal band.

6. A sensor as claimed in claim 1 or 2, wherein the exposed surface region of the electrode consists of a plurality of individual surfaces areas arranged in a matrix configuration.

7. A sensor as set forth in claim 1, wherein said sensor includes a body part and a mounting part assemblage, said body part including said sensing electrode, said mounting part including a mounting surface for engaging said body surface and having an opening therein for receiving electrolyte, said body part cooperating with said mounting part upon assembly to position said sensing electrode adjacent said opening with a predetermined spacing between said surface area and the plane of said mounting surface and to provide said electrolyte layer of predetermined thickness.

* * * * *